(12) United States Patent
Edelson

(10) Patent No.: US 8,524,495 B2
(45) Date of Patent: Sep. 3, 2013

(54) METHODS FOR INDUCING THE DIFFERENTIATION OF BLOOD MONOCYTES INTO FUNCTIONAL DENDRITIC CELLS

(75) Inventor: Richard Leslie Edelson, Westport, CT (US)

(73) Assignee: Yale University, New Haven, CT (US)

( * ) Notice: Subject to any disclaimer, the term of this patent is extended or adjusted under 35 U.S.C. 154(b) by 357 days.

(21) Appl. No.: 12/771,612

(22) Filed: Apr. 30, 2010

(65) Prior Publication Data

US 2010/0267137 A1 Oct. 21, 2010

(51) Int. Cl.
*C12N 5/07* (2010.01)
*C12N 5/0784* (2010.01)

(52) U.S. Cl.
USPC ............................ 435/377; 435/372; 435/325

(58) Field of Classification Search
USPC .......................................... 435/377, 372, 325
See application file for complete search history.

(56) References Cited

U.S. PATENT DOCUMENTS

| | | | |
|---|---|---|---|
| 4,321,918 A | 3/1982 | Clark, II | |
| 4,683,889 A | 8/1987 | Edelson | |
| 4,838,852 A | 6/1989 | Edelson et al. | |
| 6,008,040 A | 12/1999 | Datar | |
| 6,194,204 B1 | 2/2001 | Crawford et al. | |
| 6,524,855 B2 | 2/2003 | Edelson et al. | |
| 6,596,275 B1 | 7/2003 | Bartholeyns et al. | |
| 6,602,709 B1 | 8/2003 | Albert et al. | |
| 6,800,300 B1 | 10/2004 | Miller et al. | |
| 2002/0051771 A1 | 5/2002 | Bolton et al. | |
| 2002/0114793 A1 | 8/2002 | Edelson et al. | |
| 2003/0133914 A1 | 7/2003 | Edelson et al. | |
| 2003/0219420 A1 | 11/2003 | Edelson et al. | |
| 2005/0084966 A1 | 4/2005 | Edelson et al. | |
| 2006/0226057 A1 | 10/2006 | Robinson et al. | |
| 2007/0100272 A1 | 5/2007 | Briggs | |
| 2007/0281354 A1 | 12/2007 | Edelson et al. | |
| 2008/0094610 A1 | 4/2008 | Muller | |
| 2009/0053251 A1 | 2/2009 | Pogue-Caley et al. | |

FOREIGN PATENT DOCUMENTS

| | | |
|---|---|---|
| WO | 91/13632 | 9/1991 |
| WO | 93/20185 | 10/1993 |
| WO | 94/11016 | 5/1994 |
| WO | 97/34472 | 9/1997 |
| WO | 99/38380 | 8/1999 |
| WO | 00/62818 A1 | 10/2000 |

OTHER PUBLICATIONS

Elangbam et al. Cell Adhesion Molecules-Update. Vet Pathol 34:61-73 (1997).*
Charo et al. The Vitronectin Receptor alphavbeta3 Binds Fibronectin and Acts in Concert with alpha5beta1 in Promoting Cellular Attachment and Spreading on Fibronectin. The Journal of Cell Biology, vol. 111 (No. 6, Pt. 1), Dec. 1990 2795-2800.*
Miller et al. Identification and in vivo efficacy of small-molecule antagonists of integrin avb3 (the vitronectin receptor). DDT vol. 5, No. 9 Sep. 2000, p. 397-408.*
Skoberne et al. Apoptotic Cells at the Crossroads of Tolerance and Immunity. CTMI (2005) 289:259-292.*
NCBI protein database search report for vibronectin. downloaded on Jun. 22, 2012 from www.ncbi.nlm.nih.gov/protein?term=vibronectin. p. 1.*
International Search Report, Jul. 18, 2011, PCT/US11/34603.
Berger, Carole L., et al: "The growth of cutaneous T-cell lymphoma is stimulated by immature dendritic cells." Blood Apr. 15, 2002, vol. 99, No. 8, Apr. 15, 2002, pp. 2929-2939, XP002555202 ISSN: 0006-4971 p. 2934, right-hand column, paragraph 2—p. 2936, left-hand column.
Salskov-Iversen, Maria, et al.: "Rapid construction of a dendritic cell vaccine through physical pertubation and apopptotic malignant T cell loading." Journal of Immune Based Therapies and Vaccines Jul. 19, 2005, vol. 3, Jul. 19, 2005, p. 4, XP021008598 ISSN: 1476-8518 the whole document.
Supplementary European Search Report dated Nov. 27, 2009 for European Patent Application EP 05 80 2479.
Legitimo, A., et al., "In vitro treatment of monocytes with 8-methoxypsolaren and ultraviolet A light induces dendritic cells with a tolerogenic phenotype.", Clinical and Experimental Immunology, 2007, vol. 148, pp. 564-572; See the summary; p. 565, 1st column, lines 36-55; p. 569, 2nd column, line 3—p. 571, 1st column, line 12.
Girardi, M., et al., "Transimmunization and the evolution of extracorporeal photochemotherapy". Transfusion and Aphresis Science, 2002, vol. 26, pp. 181-190. See abstract.
Berger, C.L., et al., "Transimmunization, a novel approach for tumor immunotherapy". Transfusion and Aphresis Science, 2002, vol. 26, pp. 205-216.
International Search Report in International Application No. PCT/US2009/035210 mailed Sep. 11, 2009.
Jacob, et al., 2002, Monocyte-macrophage differentiation in vitro: Modulation by extracellular matrix protein substratum. Molecular and Cellular Biochemistry 233: 9-17/.
Hosein, et al., 1985. Monocyte Receptors for Fibronectin Characterized by a Monoclonal Antibody That Interferes With Receptor Activity. J. Exp. Med. vol. 162: 167-170.
White, et al., 2001, Monocyte-Fibronectin Interactions, Via a5b1 Integrin. Induce Expression of CXC Chemokine-Dependent Angiogenic Activity. The Journal of Immunology, 167: 5362-5366.
Birdsall et al., 2005, Monocytes Stimulated by 110-kDa Fibronectin Fragments Suppress Proliferation of Anti-CD3-Activated T Cells. The Journal of Immunology, 175: 3347-3353.
International Search Report, Aug. 22, 2008, PCT/US08/63911.

(Continued)

*Primary Examiner* — Taeyoon Kim
(74) *Attorney, Agent, or Firm* — McCarter & English, LLP

(57) ABSTRACT

Methods are provided for treating blood monocytes to produce functional antigen presenting dendritic cells. An extracorporeal quantity of a subject's blood is treated to separate the blood into a plasma component containing proteins, a platelet component and a buffy coat component. A plastic treatment device is provided having plastic channels that allow transmittance of light to the interior of the plastic device and a light source that produces light of a wave length selected to activate the photoactivatable agent. The plasma component containing proteins is first pumped through the plastic treatment device, followed by the platelet component and finally the buffy coat component. The resulting treated cells may be incubated or reinfused directly to the subject.

12 Claims, 2 Drawing Sheets

(56) References Cited

OTHER PUBLICATIONS

Akagawa, et al., Generation of CDI=ReIB=Dendritic Cells and Tartrate-Resistant Acid Phosphatase-Psitive Osteoclast-Like Multinucleated Giant From Human Monocytes, 1996; Blood vol. 88 No. 10:4029-4039.

Edelson, Light-Activated Drugs, Scientific American, Aug. 1988, pp. 68-75.

UVAR Photopheresis System, 1999. p. 1-11.

PCT Notification of Transmittal of the International Search Report, dated Aug. 9, 2000. PCT/US00/08793.

Isolation and Function of Human Dendritic Cells by Lisa Williams, et al.; Copyright 1999, International Review of Cytology, vol. 153; p. 41-103.

Dendritic Cells: Origin and Differentiation by Ranjeny Thomas, et al., Stem Cells. 1996; 14:196-206.

Article published in the Journal of Immunology, entitled—TGF-1 Promotes In Vitro Generation of Dendritic Cells, etc. by Elisabeth Riedl, et al., vol. 158/Np4/Feb. 15, 1997.

Article published in the Journal of Immunology, entitled TGF-B1 Promotes In Vitro Development of Dendritic Cells, etc, by Herbert Strobl, dated Aug. 15, 1996, 157:1499-1507.

Contrasting Effects of IL-4 and CD40 Ligan on the In Vitro Differentiation of Hyman Dendritic Cells, etc. by B. Canque, et al., date Nov. 15, 1997, published in Blood Magazine by A. Garbe, at al., dated Nov. 15, 1998. vol. 92, No. 10 Supplement (Part 1 of 2).

Abstract #668 from an article entitled: Transforming Growth Factor, etc. published in Blood Magazine by A. Garbe, et al., dated Nov. 15, 1997, vol. 92, No. 10 Supplement 1 Part of 2).

Flt3 Ligand in Cooperation with Transforming Growth Factor, etc. by Herbert Strobl, et al., published in Blood Magazine, vol. 90, No. 4, dated Aug. 15, 1997. pp. 1425-1434.

Berger, et al., Induction of human tumor-loaded dendritic cells, 2001, Int. J. Cancer, vol. 91, pp. 438-447.

Berger, C., et al.: "Photopheresis induces monocyte differentiation into functional dendritic antigen presenting cells", Journal of Investigative Dermatology, vol. 112, No. 4, Apr. 1999, p. 580, XP009028191.

Glass, et al.: "Cutaneous T-cell lymphoma", p. 1-13, downloaded on Jun. 26, 2007 from http://moffitt.org/moffittapps/ccj/v5n1/article.html.

International Search Report, Mar. 28, 2005, PCT/US04/07774.

Cohen, et al. CD4+CD25+ Immunoregulatory T Cells: New Therapeutics for Graft-Versus-Host Disease, The Rockefeller University Press, vol. 196, No. 3, Aug. 5, 2002, pp. 401-406.

Chambers, The expanding world of co-stimulation: the two-signal model revised, Trends in Immunology, vol. 22, No. 4, Apr. 2001, pp. 217-223.

Hoffmann, et al. Donor-type CD4+CD25+ Regulatory T Cells Suppress Lethal Acute Graft-Versus-Host Disease after Allogeneic Bone Marrow Transplantation, The Rockefeller University Press, vol. 196, No. 3, Aug. 5, 2002, pp. 389-399.

Rossi, M. et al., Plasmacytoid Dendritic Cells: Do They Have a Role in Immune Responses After Hematopoietic Cell Transplantation? Human Immunology Dec. 2002, vol. 63, No. 12, pp. 1194-1200.

Heshmati, F. Mechanisms of Action of Extracorporeal Photochemotherapy Transfusion and Apheresis Science Aug. 2003, vol. 29, No. 1, pp. 61-70, Abstract.

Ying G et al: "Tricyclic antidepressants prevent the differentiation of monocytes into macrophage-like cells in vitro." Cel Biol Toxicol 2002; 18(6):425-37.

Beaudoin L et al: "NKT cells inhibit the onset of diabetes by impairing the development of pathogenic T cells specific for pancreatic beta cells." Immunity. Dec. 2002; 17(6):725-36 (Abstract Only).

Kitazawa T et al: "Studies on delayed systemic effects of ultraviolet B radiation on the induction of contact hypersensitivity, 3. Dendritic cells from secondary lymphoid organs are deficient in interleukin-12 production and capacity to promote activation and differentiation of T helper type 1 cells." Immunology. Feb. 2000;99(2):296-304 (Abstract Only).

Tang A et al: "Inhibition of epidermal Langerhans cell function by low dose ultraviolet B radiation. Ultraviolet B radiation selectively modulates ICAM-1 (CD54) expression by murine Langerhans cells." J Immunol. May 15, 1991;146(10):3347-55 (Abstract Only).

Shen W et al: "Ganglioside GD1a impedes lipopolysaccharide-induced maturation of human dendritic cells." Cell Immunol. Dec. 2002;220(2):125-33 (Abstract Only).

Lateef Z et al: "Orf virus-encoded interleukin-10 inhibits maturation, antigen presentation and migration of murine dendritic cells." J Gen Virol. May 2003;84(Pt5):1101-0 (Abstract Only).

Shurin MR et al: "Inhibition of CD40 expression and CD-40-mediated dentritic dell function by tumor-derived IL-10." Int J Cancer. Sep. 1, 2002;101(1):61-8 (Abstract Only).

Semnani RT et al: "Filarial antigens impair the function of human dendritic cells during differentiation." Infect Immun. Sep. 2001;69(9):5313-22 (Abstract Only).

Chung F: "Anti-inflammatory cytokines in asthma and allergy: interleukin-10, interleukin-12, interferon-gamma." Mediators Inflamm. Apr. 2001;10(2):51-9. Links (Abstract Only).

Hackstein H et al: "Aspirin inhibits in vitro maturation and in vivo immunostimulatory function of murine myeloid dentritic cells." J Immunol. Jun. 15, 2001;166(12):7053-62 (Abstract Only).

Komi J et al: "Non-steroidal anti-oestrogens inhibit the differentiation of synovial macrophages into dendritic cells." Rheumatology (Oxford). Feb. 2001;40(2):185-91(Abstract Only).

Moore KW et al: "Interleukin-10 and the interleukin-10 receptor." Annu Rev Immunol. 2001;19:683-765 (Abstract Only).

Bernstein SH et al: "A randomized phase II study of BB-10010: a variant of human macrophage inflammatory protein-1 alpha for patients receiving high-dose etoposide and cyclophosphamide for malignant lymphoma and breast cancer." Br J Haematol. Dec. 1997;99(4):888-9 (Abstract Only).

Askenase PW et al: "Gamma delta T cells in normal spleen assist immunized alpha beta T cells in the adoptive cell transfer of contact sensitivity. Effect of *Bordetella pertussis*, cyclophosphamide, and antibodies to determinants on suppressor cells." J Immunol. Apr. 15, 1995;154(8):3644-53 (Abstract Only).

De Smedt T et al: "Effect of interleukin-10 on dendritic cell maturation and function." Eur J Immunol. May 1997;27(5):1229-35 (Abstract Only).

Hirohata S: "Suppression of human B cell responsiveness by CD4+ T cells does not involve CD95-CD95 ligand interactions." Cell Immunol. Nov. 1, 1997;181(2):182-91 (Abstract Only).

Estry DW et al: "A comparison of the fibrinogen receptor distribution on adherent platelets using both soluble fibrinogen and fibrinogen immobilized on gold beads." Eur J Cell Biol. Apr. 1991;54(2):196-210 (Abstract Only).

Blank K et al: "Self-immobilizing recombinant antibody fragments for immunoaffinity chromatography: generic, parallel, and scalable protein purification." Protein Expr Purif. Mar. 2002:24(2):313-22 (Abstract Only).

Garlie NK et al: "T cells activated in vitro as immunotherapy for renal cell carcinoma: characterization of 2 effector T-cell populations." J Urol. Jul. 2001;166(1):299-303 (Abstract Only).

Foger N et al: "CD44 supports T cell proliferation and apoptosis by apposition of protein kinases." Eur J Immunol Oct. 2000;30(10):2888-99 (Abstract Only).

Hanau D et al: "A method for the rapid isolation of human epidermal Langerhans cells using immunomagnetic microspheres." J Invest Dermatol. Sep. 1988;91(3):274-9 (Abstract Only).

Thomas R et al: "Human peripheral blood dendritic cell subsets. Isolation and characterization of precursor and mature antigen-presenting cells." J. Immunol. Nov. 1, 1994;153(9):4016-28 (Abstract Only).

Yanagihara S et al: "EBI1/CCR7 is a New Member of Dendritic Cell Chemokine Receptor That is Up-Regulated Upon Maturation." The Journal of Immunology 1998; 161: 3096-3102.

Li B et al: "Pretreatment of recipients with mitomycin-C-treated dendritic cells induces significant prolongation of cardiac allograft survival in mice." Transplantation Proceedings vol. 34, Issue 8, Dec. 2002, pp. 3426-3428.

Hawiger D et al: "Dendritic Cells Induce Peripheral T Cell Unresponsiveness Under Steady State Conditions In Vivo." The Journal of Experimental Medicine, vol. 194, No. 6, Sep. 17, 2001, 769-780.

Jiga L et al: "Generation of tolerogenic dendritic cells by treatment with mitomycin c: inhibition of allogeneic T-cell response is mediated by downregulation of ICAM-1, CD80, and CD86." Transplantation. vol. 77(11), Jun. 15, 2004, pp. 1761-1764.

Tanigawa T et al: "Injection of mitomycin-C-treated spleen cells induces donor-specific unresponsiveness to cardiac allografts in rats [experimental transplantation]." Transplantation. vol. 67(5), Mar. 15, 1999, pp. 653-658.

Albert M et al: "Immature Dendritic Cells Phagocytose Apoptotic Cells via $av\beta5$ and CD36, and Cross-present Antigens to Cytotoxic T Lumphocytes" J. Exp. Med. vol. 188, No. 7, Oct. 5, 1998 1359-1368.

Morel A et al: "Regulation of major histocompatability complex case II synthesis by interleukin-10." Immunology 2002 106 229-236.

Kakumu S et al: "Decreased function of peripheral blood dendritic cells in patients with hepatocellular carcinoma with hepatitis B and C virus infection." Journal of Gastroenterology and Hepatology, 2000 15, 31-436.

Coates P et al: "Human myeloid dendritic cells transduced with an adenoviral interleukin-10 gene construct inhibit human skin graft rejection in humanized NOD-scid chimeric mice." Gene Therapy, 2001 8, 1224-1233.

Corinti S et al: "Regulatory Activity of Autocrine IL-10 on Dendritic Cell Functions." J Immunol. 2001, 166: 4312-4318.

Griffin M et al: "Dendritic cell modulation by $1\alpha,25$ dihydroxyvitamin D3 and its analogs: A vitamin D receptor-dependent pathway that promotes a persistent state of immaturity in vitro and in vivo." PNAS Jun. 5, 2001 vol. 98, No. 12, 6800-6805.

Canning M et al: "$1\alpha,25$-Dydroxyvitamin D3 (1,25(OH)2D3) hampers the maturation of fully active immature dendritic cells from monocytes." European Journal of Endocrinology 2001 145 351-357.

Simon JC et al: "UVB-Irradiated Dendritic Cells Induce Nonproliferating, Regulatory Type T Cells." Skin Pharmacol Appl Skin Physiol 2002:15:330-334.

Fay, et al, Dendritic cell immunotherapy of metastatic melanoma using CD34+ hemotopietic progenitor-derived dendritic cells (CD34-DC) induced immune responses to melanoma antigen and resulted in clinical regression of metastatic disease, Blood, Nov. 16, 2000, vol. 96, p. 807a.

PCT/US02/25703 International Preliminary Examination Report, dated May 10, 2005.

Russell-Jones, R. "Shedding Light on Photophersis", The Lancet. Mar. 17, 2001, vol. 357, pp. 820-821.

Greinix, et al., "Successful Use of Extracorporeal Photochemotherapy in the Treatment of Severe Acute and Chronic Graft-Versus-Host Disease", Blood, vol. 92, No. 9, 1998, pp. 3098-3104.

Greinix, et al., Extracorporeal Photochemotherapy in the Treatment of Severe Acute and Chronic Graft-Versus-Host Disease: A Pilot Study, Blood, vol. 96, No. 7, 2000, pp. 2426-2431.

Barr, et al., "Photopheresis for the Prevention of Rejection in Cardiac Transplantation", The New England Journal of Medicine, 1998, pp. 1744-1751.

Yarmane, et al., "Suppression of Anit-Skin-Allograft Response by Photodamages Effector Cells—The Modulating Effects of Prednisolone and Cyclophosphamide", Transplantation, 1992, pp. 119-124.

Perez, "Induction of a Cell-Transferable Suppression of Alloreactivity by Photodamages Lymphocytes", Transplantation, 1992, pp. 896-903.

Perez, "DNA Associated with the Cell Membrane is Involved in the Inhibition of the Skin Rejection Response in the Inhibition of the Skin Rejection Response Induced by Infusions of Photodamaged Alloreactive Cells that Mediate Rejection of Skin Allograft", Photochemistry and Photobiology, vol. 55, No. 6, 1992, pp. 839-849.

International Preliminary Report on Patentability for International Application No. PCT/US2011/034603, dated Nov. 6, 2012.

* cited by examiner

METHODS FOR INDUCING THE DIFFERENTIATION OF BLOOD MONOCYTES INTO FUNCTIONAL DENDRITIC CELLS

FIELD OF THE INVENTION

The present invention relates to methods for producing functional antigen presenting dendritic cells. The dendritic cells are produced by treating an extracorporeal quantity of a subject's blood using a process referred to herein as transimmunization to induce blood monocytes to differentiate into dendritic cells. The functional antigen presenting dendritic cells may be administered to a subject to induce cellular immunologic responses to disease causing agents.

BACKGROUND

Dendritic cells (DCs) are recognized to be powerful antigen presenting cells for inducing cellular immunologic responses in humans, and play a key role in eliciting effective anti-tumor immune responses. DCs prime both CD8+cytotoxic T-cell (CTL) and CD4+T-helper (Th 1) responses. DCs are capable of capturing and processing antigens, and migrating to the regional lymph nodes to present the captured antigens and induce T-cell responses. In humans, DCs are a relatively rare component of peripheral blood (<1%), but large quantities of DCs can be differentiated from CD34+ precursors or blood monocytes utilizing expensive cytokine cocktails. Alternatively, by treating an extracorporeal quantity of blood using a process referred to herein as trans immunization, a large number of immature DCs can be induced to form from blood monocytes without the need for cytokine stimulation. These immature DCs can internalize and process materials from disease effectors, such as antigens, DNA or other cellular materials, to induce cellular immunologic responses to disease effectors. By exposing increased numbers of dendritic cells to cellular material, such as for example antigens from tumor or other disease-causing cells, followed by reintroduction of the loaded dendritic cells to the patient, presentation of the cellular material to responding T-cells can be enhanced significantly.

For example, one in vitro method previously used involves culturing blood mononuclear leukocytes for six to eight days in the presence of granulocyte-monocyte colony stimulating factor (GM-CSF) and interleukin-4 (IL-4) to produce large numbers of dendritic cells. These cells can then be externally loaded with tumor-derived peptide antigens for presentation to T-cells. Alternatively, the dendritic cells can be transduced to produce and present these antigens themselves. Expanding populations of dendritic cells transduced to produce and secrete cytokines which recruit and activate other mononuclear leukocytes, including T-cells, has shown some clinical efficacy in generating anti-tumor immune responses.

However, transducing cultivated dendritic cells to produce a particular generic antigen and/or additional cytokines is labor intensive and expensive. More importantly, when used to treat a disease such as cancer, this procedure likely fails to produce and present those multiple tumor antigens that may be most relevant to the individual's own cancer. Several approaches have been proposed to overcome this problem. Hybridization of cultivated autologous dendritic cells with tumor cells would produce tetraploid cells capable of processing and presenting multiple unknown tumor antigens. In a second proposed approach, acid elution of Class I and Class II major histocompatability complexes (MHC) from the surface of malignant cells would liberate a broad spectrum of tumor-derived peptides. These liberated peptides could then be externally loaded onto MHC complexes of autologous cultivated dendritic cells.

Because there are limitations to each of these approaches, an improved method of producing functional antigen presenting dendritic cells and for loading the dendritic cells with cellular material from disease causing agents is desirable. In U.S. Pat. Nos. 6,524,855, 6,607,722 and 7,109,031, the entire contents of each of which are hereby incorporated by reference, methods of producing increased numbers of functional dendritic cells are described. The methods described in these patents generally involve exposure of blood monocytes to internal surfaces of a plastic treatment device. As the blood monocytes flow past the plastic surface of the treatment device, interaction with the plastic surface induces differentiation of the monocytes into dendritic cells. The dendritic cells may then be incubated with apoptotic disease cells to produce antigen presenting dendritic cells. These methods typically produce mature dendritic cells which can be used to enhance the immune response to disease cells.

In U.S. patent application Ser. No. 10/290,802, the entire contents of which are hereby incorporated by reference, methods of producing immunosuppressive dendritic cells are described. Dendritic cells are produced by treating monocytes in a plastic treatment device as described above. The maturation of the dendritic cells is truncated at a stage where the dendritic cells are immunosuppressive.

While the methods described in these references are effective in producing relatively large numbers of dendritic cells, it would be desirable to have a process that further increases the number of dendritic cells produced from a quantity of a patient's blood. It would also be desirable to control the process to produce the desired types of dendritic cells (i.e. immune enhancing or immunosuppressive).

Accordingly, it is an object of the present invention to provide methods to produce large quantities of dendritic cells having desired functionality as immune enhancing or immunosuppressive. Other objectives and advantages of the present invention will be apparent to one skilled in the art based upon the description of preferred embodiments set forth below.

SUMMARY OF THE INVENTION

A large number of immature dendritic cells are created by treating a quantity of a patient's blood containing monocytes by flowing the blood through narrow plastic channels in a process referred to herein as transimmunization. The monocytes interact with the surface of the plastic treatment device and/or serum proteins and platelets adhered to the walls of the plastic treatment device. The interaction of the monocytes with the surfaces and/or serum proteins and platelets induces the monocytes to differentiate to form functional dendritic cells.

In a first aspect, the methods of the invention comprise pumping extracorporeal blood from a patient through a plastic treatment device, such as for example a conventional photopheresis device. The serum proteins in the blood, such as fibronectin and fibrinogen, adhere to the walls of the plastic treatment device, and monocytes in the blood interact with the plastic surfaces and the adhered serum proteins to induce monocyte differentiation.

In another aspect, the methods of the invention comprise separating the plasma containing proteins from the fraction containing blood monocytes. The plasma containing proteins, such as fibronectin and fibrinogen, is first pumped through the plastic treatment device to coat the surfaces of the treatment device with proteins. The fraction containing monocytes is then pumped through the plastic treatment device. This increases the exposure of the monocytes to proteins adhered to the walls of the plastic treatment device to enhance differentiation of the monocytes into dendritic cells.

In yet another aspect, the invention relates to a method of treating a extracorporeal quantity of blood by first separating the blood in a leukapheresis device and pumping the separated blood components sequentially through a plastic treatment device. In this embodiment of the invention, an extracorporeal quantity of a subject's blood is obtained and treated by leukapheresis to separate the blood into a plasma component containing proteins, a platelet component and a buffy coat component. A plastic treatment device having channels is used to treat the blood components. The plastic treatment device may allow transmittance of light to the interior of the plastic device and include a light source that produces light of a wavelength selected to activate a photoactivatable agent.

The plasma component containing proteins is first pumped through the plastic treatment device to coat the surface of the device with plasma proteins, including fibronectin and fibrinogen. The plasma proteins adhere to the walls of the plastic treatment device. The flow rate of the plasma component through the plastic treatment device is controlled to obtain a desired level of protein adherence to the plastic surfaces. If desired, the flow can be stopped for a period of time and the plasma component can "soak" the surfaces of the plastic treatment device.

The platelet component is next pumped through the plastic treatment device. The platelets interact with the plastic treatment device and the proteins adhered to the walls of the plastic treatment device. The flow rate of the platelet component through the plastic treatment device is controlled to obtain a desired level of platelet interaction. If desired, the flow can be stopped for a period of time and the platelet component can "soak" in the plastic treatment device.

Finally, the buffy coat component containing monocytes is pumped through the plastic treatment device. The monocytes interact with the platelets and plasma proteins to induce a high percentage of the monocytes to differentiate into functional dendritic cells. The flow rate of the monocytes through the plastic treatment device is controlled to obtain the desired level of monocyte interaction with the proteins and platelets on the surface of the plastic treatment device. By controlling the flow rate through the treatment device and the amount of light to which the cells are exposed, the maturation of the dendritic cells produced can be controlled to obtain dendritic cells having the desired functionality.

The treated buffy coat component may, if desired, be incubated for a sufficient time to allow the formation of functional dendritic cells, and then be reinfused to the patient. In one embodiment, the treated cells may be incubated at a temperature of between 35 degrees to 40 degrees Centigrade for a period of up to 48 hours.

In yet another aspect, the treated monocytes are co-incubated with apoptotic disease effector cells before reinfusing the cells to the patient. The disease effector cells may be rendered apoptotic by treating the extracorporeal quantity of blood with a photoactivatable agent, for example a psoralen such as 8-MOP, and exposing the blood to an appropriate wavelength of light as the blood passes through the plastic treatment device. Alternatively, The disease effector agents may be rendered apoptotic separately and added to the treated monocytes for co-incubation. The dendritic cells formed from the treated monoyctes phagocitize the apoptotic disease effector cells. Following co-incubation, the antigen loaded dendritic cells may be infused to the patient.

DETAILED DESCRIPTION OF PREFERRED EMBODIMENTS

Figure 1:
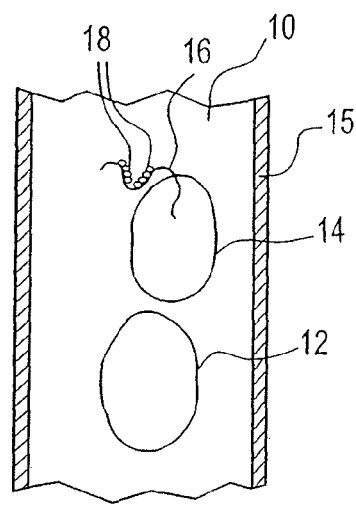
FIG. 1 is a cross-sectional view of a plastic channel containing a blood monocyte from the subject's blood illustrating a CTCL cell with a class I associated antigen, and a blood monocyte.

The present invention is directed to improved methods of producing functional dendritic cells from blood monocytes. Monocyte differentiation may be induced by physical perturbation resulting from interaction with plastic surfaces, interaction with blood components adhered to the surfaces of a plastic treatment device, or both phenomena working in a complementary manner.

As described previously in, for example, U.S. Pat. No. 7,109,031, the entire contents of which are hereby incorporated in their entirety, monocyte differentiation may be initiated by exposing the monocytes contained in an extracorporeal quantity of a subject's blood to the physical forces resulting from the sequential adhesion and release of the monocytes on plastic surfaces, such as the surfaces of the channels of a conventional photopheresis device or another type of plastic treatment device designed for this process. Monocytes are attracted to the plastic channel walls of the photopheresis apparatus, and the monocytes adhere to the channel walls. The fluid flow through the channel imposes shearing forces on the adhered monocytes that cause the monocytes to be released from the plastic channel walls. Accordingly, as the monocytes pass through the photopheresis apparatus, they may undergo several episodes of adherence to and release from the plastic channel walls. These physical forces send activation signals though the monocyte cell membrane, which results in induction of differentiation of monocytes into immature dendritic cells that are phagocytic.

In another embodiment of the invention, monocyte differentiation is induced utilizing the adherence of certain serum proteins to the plastic treatment device, such as, for example, fibronectins, fibrinogen or vitronectins, to induce differentiation of the monocytes. Monocyte differentiation into dendritic cells can be initiated by signals received through the cell membrane. Fibronectins, fibrinogen and vitronectins are proteins contained in plasma of the bloodstream. These serum proteins can provide signals to monocytes, after binding monocyte membrane receptors, helping to stimulate monocyte differentiation into dendritic cells. In vivo, one of the functions of proteins such as fibronectin, fibrinogen and vitronectin is to adhere to the cells lining the inner surface of blood vessels. As blood containing monocytes flows past the protein bearing vessel wall, monocytes contained in the blood come into contact with and adhere to the protein, an initial step contributing to the capacity of these white blood cells to leave the blood vessels and migrate into the surrounding tissue. The monocytes accomplish this migration by pulling themselves, by a process known as "diapedesis," between the endothelial cells which line the capillaries and other blood vessels. The transmigratory process, abetted by the binding of fibronectins, fibrinogen, vitronectins and related proteins, to monocyte membrane receptors, contributes to the maturation of monocytes into dendritic antigen presenting cells, capable of stimulating often specific immune reactions.

It has been discovered that serum proteins such as fibronectin, fibrinogen and vitronectin contained in blood plasma will also adhere to the surface of plastics, such as those used in a photopheresis device or in a plastic treatment device constructed to treat blood in the transimmunization process as described further below. The fibronectin, fibrinogen and vitronectin adhered on the surface of the plastic transmits signals to monocytes flowing past the proteins causing the monocytes to differentiate into dendritic cells. The differentiation of monocytes is enhanced in the transimmunization process because of the large plastic surface accessible to a large number of monocytes procured through this extracorporeal procedure. The interaction of the passaged monocytes to the proteins adherent to the plastic surface is reminiscent of the in vivo interaction of monocytes with proteins adherent to endothelial cells of blood vessels. Similarly, the stimulation of monocyte maturation into dendritic cells through such interaction with serum proteins such as fibronectin, fibrinogen or vitronectin coating the surface of the plastic treatment device is reminiscent of the in vivo maturation of monocytes into dendritic cells, as contributed to by this process in intact mammals. As a result, a large number of processed blood monocytes can be stimulated to become dendritic cells, entering this maturational pathway within one day after being so processed. These newly formed dendritic cells have various therapeutic uses, enhanced by the synchronicity of their level of maturation. It should be noted that this process may work in conjunction with, and be complementary to, physical perturbation of the monocytes in the treatment device to induce differentiation of blood monocytes into dendritic cells.

Because serum proteins such as fibronectin, fibrinogen and vitronectin are abundantly found in plasma, the plastic surfaces of the device used for the transimmunization procedure are readily exposed to the proteins during the photopheresis process. To coat the plastic surface with proteins such as fibronectin, fibrinogen and vitronectin, it is important that the blood containing plasma be pumped through the treatment device. Monocytes can be simultaneously pumped through the treatment device together with the plasma containing the serum proteins. Alternatively, the monocytes can be separated from the plasma, and the plasma may be pumped through the treatment device to condition the plastic surface with proteins such as fibronectin, fibrinogen and vitronectin. The proteins adhere to the surface of the plastic, and the monocytes are then pumped through the treatment device and pass close to the protein conditioned plastic. The monocytes receive a signal from the proteins to contribute to their differentiation into functional dendritic cells.

In one embodiment, an extracorporeal quantity of blood is obtained from a subject. The extracorporeal quantity of blood is treated by conventional leukapheresis as described above to obtain a leukocyte concentrate comprising monocytes and plasma containing proteins including fibronectin, fibrinogen and vitronectin. The monocytes and protein containing plasma are pumped together through a plastic treatment device (for example, a photopheresis device or a plastic treatment apparatus of the type described below). In this embodiment, the treatment conditions, such as flow rates, temperatures and treatment times, are typically similar to those used in conventional photopheresis. Flow rates may range from 10 ml/minute to 200 ml/minute to produce shearing forces in the treatment device of between 0.1 dynes/cm$^2$ to 50 dynes/cm$^2$. It is understood, however, that one skilled in the art may alter these parameters as appropriate to achieve a desired result.

At least some of the proteins contained in the plasma adhere to the plastic surfaces and interact with passing monocytes. The proteins, in particular the fibronectin, fibrinogen and vitronectin, signal the monocytes to differentiate and form dendritic cells. Following treatment in the treatment device, the monocytes may be reinfused to the patient or may be incubated for variable times, up to three days. As described below, the monocytes may be coincubated with disease effector cells that have been rendered apoptotic or inactive to allow the dendritic cells to phagocytize the disease effector cells. The incubated monocytes may be administered to the subject or frozen for later use.

In another embodiment of the invention, a treatment device is first conditioned using blood plasma obtained from a subject to coat the surface of the device with serum proteins including fibronectin, fibrinogen and vitronectin. In this embodiment, the extracorporeal quantity of blood is first treated using a leukapheresis device to obtain a leukocyte concentrate. The leukocyte concentrate is then further treated to separate the blood cells, including the monocytes, from the plasma. This treatment step can be performed using any technique known to those skilled in the art, such as for example using centrifugal elutriation, a density gradient or by immunoselection.

The plasma component containing proteins including fibronectin, fibrinogen and/or vitronectin is pumped through the treatment device to condition the plastic surfaces of the device with the proteins. The quantity of plasma pumped through the device is selected to achieve a desired level of fibronectin, fibrinogen and/or vitronectin adhered to the plastic surface. The can be determined based upon the concentration of the proteins in the plasma and the surface area of the plastic surface. In this embodiment, the plasma is pumped through the treatment device under conditions (temperature, flow rates, volumes, etc.) such as those described above. It is understood, however, that one skilled in the art may alter these parameters as required to achieve a desired result. At least some of the fibronectin, fibrinogen and vitronectin in the plasma adheres to the plastic surface. Monocytes obtained from the extracorporeal quantity of blood are then pumped through the treatment device where they are exposed to the proteins adhered to the surface of the plastic. The fibronectin, fibrinogen and vitronectin signals the monocytes to differentiate and form dendritic cells. After passing through the treatment device, the monocytes may be incubated to allow differentiation of the monocytes to proceed. If desired, the monocytes may be co-incubated with disease effector cells that have been rendered apoptotic or inactive as described above. The incubated monocytes may be administered to the subject or frozen for later use.

In another embodiment of the invention, an extracorporeal quantity of blood is treated by leukapheresis to separate the blood into three components, the plasma, the platelets and the buffy coat. The plasma, which contains proteins such as fibronectin and fibrinogen, is the lightest blood fraction, and therefore is the first portion of the blood selectively removed from the centrifuge and passaged through the plastic plates of the treatment device. The proteins in the plasma, such as fibronectin and fibrinogen, adhere to and coat the surfaces of the plastic treatment device. By controlling the speed of the pump that propels the plasma through the plate, the degree of coating of the plastic treatment device can be controlled. To increase the degree of coating, the pump may be operated to slow the flow of the plasma through the treatment device. If desired, the pump may be stopped to allow the plasma proteins to remain in the plastic treatment device for an extended time and adhere to the surfaces of the plastic treatment device. In one embodiment, the plasma is exposed to the plastic surfaces in the treatment device for a period between about 1 to 60 minutes. To enhance plasma protein adherence to the plastic surfaces of the plate, the flow may be temporarily discontinued (for up to 60 minutes), before resumption, or the flow rate may be slowed from the filling rate (up to 100 ml/minute) to as low as 5 ml/minute, during this phase of the procedure. This, and the other relevant variations in flow rate described for the other phases of the process, is a major departure from the steady rapid flow rates currently operative in extracorporeal photopheresis (ECP).

After the plasma has been pumped through the plastic treatment device and the plastic surfaces have been coated with proteins, the second lightest component in the leukapheresis centrifuge, the platelet fraction, is pumped into and through the plastic treatment device. The platelets bind either directly to the plastic surfaces of the plastic treatment device or to the proteins which have adhered to the surface of the plastic treatment device, in particular to the fibrinogen or fibronectin. It is noteworthy that both of these proteins, as well as several others, contain repetitive tripeptide segments (RGD or arginine-glycine-aspartic acid), for which platelets have specific receptors. The platelets are then pumped through the plastic treatment device at a rate that maximizes binding of the platelets to the protein. The flow rate may be adjusted upward or downward, or flow may be stopped for a period of time, to obtain the desired level of platelets bound to the protein. Typically, it will be desirable to allow 5-30 minutes for the platelets to bind to the proteins.

The third lightest fraction to be eluted from the leukapheresis centrifuge is the buffy coat, which contains the white blood cells, including the blood monocytes. The buffy coat including the monocytes is pumped through the treatment device next. The monocytes bear receptors for the adherent platelets, which hence serve as a bridge between the monocytes and the proteins adhered to the plastic surface, or the plastic surface itself. As the monocytes flow through the treatment device, they alternately bind to and disadhere from the platelets by the shearing force induced by the flow through the treatment device. The residence time of the monocyte/platelet interaction may be controlled by varying the speed of the pump. For example, the pump may initially be operated at a slow speed to enhance monocyte/platelet interaction, and the speed may then be increased to facilitate disadherence and collection of the treated monocytes from the treatment device. Adherence of the monocytes to the platelets may be best accomplished at 0.1 to 0.5 dynes/cm$^2$, while disadherence and collection of the monocytes may be best accomplished at increased shear levels of 1 to 50 dynes/cm$^2$.

The flow rate through the treatment device will also effect the differentiation of the monocytes into dendritic cells. A flow gradient is created in the channel in the plastic treatment device as the blood is pumped through. At lower flow rates, there will be a slower flow zone near the plate parallel surfaces in the treatment device. As a result, the monocytes closer to the plates in the treatment device will have substantially more interaction with the plastic-adherent platelets and proteins than the more rapidly flowing monocytes towards the center of the flow passage between the plates. The monocytes will alternately bind to and disadhere from the platelets. Maturation of monocytes into dendritic cells is greatly enhanced by this interaction, with increased exposure to the platelets thereby providing increased signaling of this maturational process.

As discussed further below, a photoactivatable agent, for example a psoralen such as 8-MOP, may be added to the blood before leukapheresis or to the buffy coat after leukaphereis, and the buffy coat component may be exposed to ultraviolet light to render disease cells in the buffy coat apoptotic. Since exposure to the ultraviolet energy, inherent in conventional ECP and Transimmunization, is greatest for those monocytes closest to the plastic surfaces, the monocytes receiving the largest level of interaction with the adherent platelets are also the ones receiving the largest exposure to ultraviolet energy and, therefore, the largest exposure to the photoactivated chemical agent, such as 8-methoxypsoralen. The photoactivated drug then truncates the maturation of the exposed monocytes, thereby tending to increase the percentage of induced "immature" dendritic cells. This is important, since the immature dendritic cells, displaying relatively low levels of co-stimulatory molecules (such as CD80 and CD86) can be efficient down-regulatory, or immunosuppressive, leukocytes. Conversely, monocytes that flow through the middle region of the flow passage mature more slowly, but more completely, since their exposure to the adherent platelets is lower, as is their exposure to the maturationally truncating photo-activated drug. The dendritic cells derived from this subset of monocytes become high expressers of the co-stimulatory molecules and evolve into immunostimulatory dendritic cells, more effective in vaccination against the antigens that they present to responding T cells.

Hence, by controlling the amount of light, flow rates and psoralen content, the types of dendritic cells formed can be controlled. For example, if the monocytes are treated without any light or psoralen, the dendritic cells will mature and become immunizing. Alternatively, if the flow rate is slow and the monocytes are exposed to psoralen and light, immunosuppressive dendritic cells will be formed. This extracorporeal system can, therefore, produce exceptionally finely titrated results.

While not being bound to any particular mechanism of action, applicant believes that non-activated platelets bind to they chain of proteins, particularly fibrinogen, activating the $\alpha_5\beta_1$ and $\alpha_{IIB}\beta_3$ integrins. Once firmly bound to the fibrinogen, the platelets express P-selectin, the ligand for PSGL-1 on inactive monocytes. The platelets bridge the monocytes to the proteins such as fibrinogen. The activated platelets, which express fibronectin and fibrinogen, can then further activate the monocytes.

EXAMPLE

An example of the embodiment described above is provided. It is desirable to produce and reintroduce to the patient a necessary number of mature dendritic cells, induced from processing of the particular patient's monocytes in the plastic treatment device. The positive impact of the sequential layering onto the plastic surface of the necessary components, followed by the elution of the incipient DC, can be more effectively accomplished by modification of resident times in the plastic treatment device, variation of flow rates through the plastic treatment device and control of when the ultraviolet energy is turned on or off to render disease cells apoptotic.

In conventional photopheresis, the flow rate is constant and the lights are on for the large majority of the blood processing. In the embodiment described above, after the extracorporeal blood is separated into three components or fractions (plasma, platelets and buffy coat), the plasma fraction is first be allowed to fill the plastic treatment device and remain static for about fifteen minutes. This permits more efficient layering of the parallel plastic surfaces with important fibrinogen, fibronectin, vitronectin and osteopontin, as well as other contributory proteins, containing components which bind and activate platelets. Of special importance, for example, fibrinogen contains a gamma chain for which passaged resting platelets have avid receptors.

After permitting sufficient time for adherence of the plasma proteins, a platelet-rich fraction will then similarly be pumped into the plastic treatment device and permitted to remain static for about fifteen minutes, to enhance the adherence of platelets to the plasma proteins and activation of the platelets. Once activated, these adherent platelets quickly strengthen their binding to relevant proteins, prominently through the binding of platelet membrane integrin receptors to repeating in tripeptide RGD segments displayed in the adherent proteins. The tightly adherent activated platelets quickly express membrane p-selectin.

The monocyte-enriched fraction is next passed through the plastic treatment device at a flow rate of about 15 cc/min to create a continuous flow force of about 0.6 dyne/cc$^2$. This is considerably less than the shear force created by the currently operative photopheresis flow rate of 40 cc/min. This flow rate and shear force enables maximal adherence and stimulation of the passaged monocytes and approximately doubles the efficiency of conversion of monocytes-to-DC (>60% as opposed to about 30%). Finally, after the full volume of the monocyte fraction has been so passaged, the flow rate is increased to a preferred 60 cc/min or greater, causing maximal dissociation of adhered monocytes from the plastic treatment device, and therefore maximal harvesting of the incipient DC. These newly formed DC can then either be immediately reinfused into the patient or, prior to re-administration, they can be further processed ex vivo, such as by loading them with immunogenic antigens (e.g. those expressed on apoptotic tumor cells or pathogenic infectious agents), stunting their maturation with photoactivated 8-MOP (increasing their immunomodulating efficiency in auto-immune clinical situations) or enhancing their maturation (increasing their efficiency in cancer immunotherapy).

By using the methods of the present invention described above, a large number of healthy dendritic cells can be formed having virtually the same maturity. When these dendritic cells are coincubated with apoptotic disease cells or other sources of antigens, the dendritic cells will display the antigens to induce a desired immune response. It is the combination of forming a large number of similarly mature dendritic cells and the incubation of these cells for a sufficient period of time with the apoptotic disease cells or antigen source that produces antigen presenting dendritic cells that are particularly effective in therapeutic use. By inducing the monocytes to differentiate into dendritic cells without using a photoactivatable drug and light, the resulting dendritic cells are particularly healthy and effective for use in immunotherapeutic applications.

In another embodiment, an extracorporeal quantity of blood from a subject is obtained for treatment. If desired, the blood may be treated by leukapheresis to obtain a white blood cell concentrate comprising monocytes, disease effector cells and plasma containing protein. A photoactivatable agent, such as for example 8-MOP, is added to the blood. The plasma containing protein is first pumped through the plastic treatment device to coat the plastic surfaces with proteins. The white blood cell concentrate is then passed through a plastic treatment device having narrow channels as described above that is capable of allowing light to pass through the walls of the device and enter the blood. Flow rates may be controlled and varied as described above. The plastic treatment device is arranged with a light source providing the light necessary to activate the photoactivatable agent. In a preferred embodiment, the plastic treatment device is a photopheresis device.

During the passage of approximately the first half of the blood through the plastic device, the light source is turned off or the light is otherwise shielded from the treatment device to prevent light from activating the photoactivatable agent, such as by a metal foil or other opaque material that will block light. During this time, monocytes in the blood interact with the internal surfaces of the device, including proteins bound to the surfaces, to induce differentiation of the monocytes into dendritic cells. Because the light source is turned off during this portion of the process, the photoactivatable agent is not activated and the monocytes are not affected in any way by the photoactivatable agent. The treated blood is stored in a blood bag following treatment.

After approximately half of the blood is passed through the plastic treatment device, the light source is turned on and the remainder of the blood is exposed to light as it passes through the treatment device. This activates the photoactivatable agent causing apoptosis of disease causing lymphocytes in the blood. While the photoactivatable agent does not induce apoptosis of all monocytes in the second portion of the blood, it may influence the development of the monocytes into dendritic cells. After passage and exposure of the second protion of the blood to the photoactivated drug in the exposure plate, this portion of the blood may be stored in a second blood bag following treatment, or it may be placed directly in the blood bag containing the first portion of the treated blood. Where a second blood bag is used, the two portions of treated blood are then combined in a single bag for incubation or for reinfusion into the patient without incubation.

In another embodiment, an extracorporeal quantity of blood from a subject is segregated into two approximately equal volumes. The blood may be treated prior to segregation by leukapheresis to obtain a white blood cell concentrate comprising monocytes, disease effector cells and plasma containing protein. The first volume of blood is treated in a plastic treatment device without a photoactivatable agent to begin induction of the differentiation of monocytes into dendritic cells. The plasma containing protein is first pumped through the plastic treatment device to coat the plastic surfaces with proteins. The white blood cell concentrate is then pumped through the plastic treatment device. Flow rates may be controlled and varied as described above. Following treatment, the first volume of blood is stored in a first blood bag. The second volume of blood is separately treated to render disease effector cells in the volume of blood apoptotic. The disease effector cells may be rendered apoptotic by any of the methods described in this application. In a preferred embodiment, the disease effector cells are rendered apoptotic by adding 8-MOP to the second volume of blood and then exposing the second volume of blood to light, as in a photopheresis device. Following treatment, the second volume of blood is stored in a second blood bag. After both volumes of blood have been treated, the two volumes are combined and incubated as described above.

Following treatment of the monocytes using any of the embodiments described above, the resulting dendritic cells may be reinfused directly to the patient, or the dendritic cells may be incubated with apoptotic disease effector agents to produce antigen presenting dendritic cells. As used herein, the term "disease effector agents" refers to agents that are central to the causation of a disease state in a subject. In certain circumstances, these disease effector agents are disease-causing cells which may be circulating in the bloodstream, thereby making them readily accessible to extracorporeal manipulations and treatments. Examples of such disease-causing cells include malignant T-cells, malignant B cells, T-cells and B cells which mediate an autoimmune response, and virally or bacterially infected white blood cells which express on their surface viral or bacterial peptides or proteins. Exemplary disease categories giving rise to disease-causing cells include leukemia, lymphoma, autoimmune disease, graft versus host disease, and tissue rejection. Disease associated antigens which mediate these disease states and which are derived from disease-causing cells include peptides that bind to a MHC Class I site, a MHC Class II site, or to a heat shock protein which is involved in transporting peptides to and from MHC sites (i.e., a chaperone). Disease associated antigens also include viral or bacterial peptides which are expressed on the surface of infected white blood cells, usually in association with an MHC Class I or Class II molecule.

Other disease-causing cells include those isolated from surgically excised specimens from solid tumors, such as lung, colon, brain, kidney or skin cancers. These cells can be manipulated extracorporeally in analogous fashion to blood leukocytes, after they are brought into suspension or propagated in tissue culture. Alternatively, in some instances, it has been shown that the circulating blood of patients with solid tumors can contain malignant cells that have broken off from the tumors and entered the circulation. [Kraeft, et al., Detection and analysis of cancer cells in blood and bone marrow using a rare event imaging system, *Clinical Cancer Research*, 6:434-42, 2000.] These circulating tumor cells can provide an easily accessible source of cancer cells which may be isolated, rendered apoptotic and engulfed by the dendritic cells in accordance with the method described and claimed herein.

In addition to disease-causing cells, disease effector agents falling within the scope of the invention further include microbes such as bacteria, fungi and viruses which express disease-associated antigens. It should be understood that viruses can be engineered to be "incomplete", i.e., produce distinguishing disease-causing antigens without being able to function as an actual infectious agent, and that such "incomplete" viruses fall within the meaning of the term "disease effector agents" as used herein.

In one embodiment of the methods described herein, the disease effector agents are presented to the dendritic cells after being rendered apoptotic. As discussed above, disease effector cells contained in the extracorporeal quantity of blood may be rendered apoptotic by adding a photoactivatable agent, such as 8-MOP, to the blood and exposing the blood to light during all or part of the treatment of the blood. Alternatively, disease effector cells may be isolated separately and treated to render them apoptotic. Any method of isolating disease cells and rendering the cells apoptotic that is known to those skilled in the art may be used. For example, disease effector agents such as cancer cells may be isolated by surgical excision of cells from a patient. Blood borne disease effector cells may be isolated from an extracorporeal quantity of a subject's blood and the isolated cells may be treated to induce apoptosis.

Apoptosis may be induced by adding photo-activated drugs to the disease cells and exposing the cells to light. Cell death can also be induced by exposure of cells to ionizing radiation, for example by exposure to gamma radiation or x-rays utilizing devices routinely available in a hospital setting. Cancer cells may be rendered apoptotic by addition of synthetic peptides with the arginine-glycine-aspartate (RGD) motif cell suspensions of the disease-causing cells isolated from the patient's blood, from excised solid tumors or tissue cultures of the same. RGD has been shown (Nature, Volume 397, pages 534-539, 1999) to induce apoptosis in tumor cells, possibly by triggering pro-capase-3 autoprocessing and activation. Similarly, apoptosis could be induced in cells having Fas receptors, by stimulating with antibodies directed against this receptor, in this way sending signals to the inside of the cell to initiate programmed cell death, in the same way that normally Fas ligand does. In addition, apoptosis can be induced by subjecting disease-causing cells to heat or cold shock, certain viral infections (i.e., influenza virus), or bacterial toxins. Alternatively, certain infectious agents such as influenza virus can cause apoptosis and could be used to accomplish this purpose in cell suspensions of disease-causing cells.

The apoptotic cells are exposed to the dendritic cells produced as described above, which internalize and process the cellular material. In one embodiment of the invention, the apoptotic cells are produced during the photopheresis procedure through the use of the drug 8-methoxypsoralen and ultraviolet A light and are collected in an incubation bag with the immature dendritic cells, and the apoptotic cells are phagocytosed by the dendritic cells during the incubation period. The resulting dendritic cells are then administered to the patient to induce an immune response to the disease causing agent.

Inducing monocytes to form dendritic cells by these methods offers several advantages for immunotherapeutic treatment. Because all of the dendritic cells are formed from the monocytes within a very short period of time, the dendritic cells are all of approximately the same age and maturation. Dendritic cells will phagocytize apoptotic cells during a distinct period early in their life cycle. In addition, the antigens present in the phagocytized apoptotic cells are processed and presented at the surface of the dendritic cells during a later distinct period. By creating dendritic cells with a relatively narrow age profile, the method of the present invention provides an enhanced number of dendritic cells capable of phagocitizing apoptotic disease effector agents and subsequently presenting antigens from those disease effector agents for use in immunotherapeutic treatment.

As discussed above, the treated monocytes may be sequestered for incubation either with or without apoptotic disease effector cells. When the treated monocytes are incubated in the presence of apoptotic cells delivered to the dendritic cells, the incubation period allows the dendritic cells forming and maturing in the blood concentrate to be in relatively close proximity to the apoptotic cells, thereby increasing the likelihood that the apoptotic cells will be engulfed and processed by the dendritic cells. A standard blood bag may be utilized for incubation of the monocytes. However, it has been found to be particularly advantageous to use a blood bag of the type which does not leach substantial amounts of plasticizer and which is sufficiently porous to permit exchange of gases, particularly $CO_2$ and $O_2$. Such bags are available from, for example, the Fenwall division of Baxter Healthcare Corp. under the name Amicus™ Apheresis Kit. Various plasticizer-free blood bags are also disclosed in U.S. Pat. Nos. 5,686,768 and 5,167,657, the disclosures of which are herein incorporated by reference.

The treated blood cell concentrate and disease effector agents are incubated for a period of time sufficient to maximize the number of functional antigen presenting dendritic cells in the incubated cell population. Typically, the treated blood cell concentrate and disease effector agents are incubated for a period of from about 1 to about 24 hours, with the preferred incubation time extending over a period of from about 12 to about 24 hours. Additional incubation time may be necessary to fully mature the loaded DC prior to reintroduction to the subject. Preferably, the blood cell concentrate and disease effector agents are incubated at a temperature of between 35 degrees Centigrade and 40 degrees Centigrade. In a particularly preferred embodiment, the incubation is performed at about 37 degrees Centigrade. By treating monocytes in the manner described above and then incubating the treated cell population with the disease effector agents, a large number of functional antigen presenting dendritic cells can be obtained. The activated monocytes produce natural cytokines which aid in the differentiation of the monocytes into dendritic cells. Alternatively, a buffered culture medium may be added to the blood bag and one or more cytokines, such as GM-CSF and IL-4, during the incubation period. Maturation cocktails (typically consisting of combinations of ligands such as CD4OL; cytokines such as interferon gamma, TNF alpha, interleukin 1 or prostaglandin E2; or stimulatory bacterial products) may be added to ensure production of fully functional mature DC.

The application of one embodiment of the method described above is illustrated in FIGS. 1 to 7. FIGS. 1 to 7 illustrate treatment of individual cells, but it should be understood that in practice a plurality of blood monocytes will be converted to dendritic cells, and that the plurality of dendritic cells will interact with a plurality of T-cells. Referring to FIG. 1, a plastic channel 10 contains a quantity of the subject's blood, or the blood cell concentrate if the subject's blood is first treated by leukapheresis. The blood contains blood monocytes 12 and is pumped through the plastic channel to induce differentiation of the monocytes into dendritic cells. The blood may also contain disease effector agents, such as, for example, a CTCL cell 14 with a class I associated antigen 16.

Figure 2:
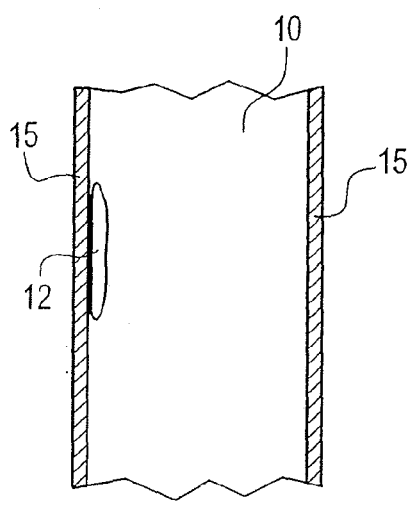
FIG. 2 is a cross-sectional view of a plastic channel containing the subject's blood illustrating a blood monocyte adhered to the wall of the plastic channel.
Figure 3:
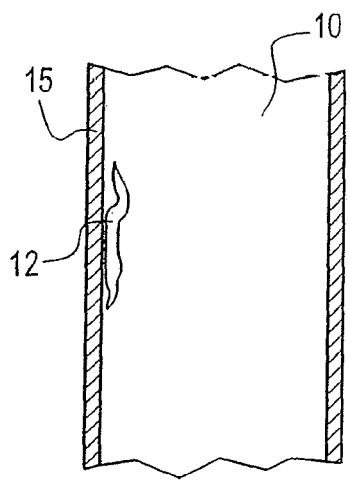
FIG. 3 is a cross-sectional view of a plastic channel containing the subject's blood illustrating a blood monocyte partially adhered to the wall of the channel.
Figure 4:
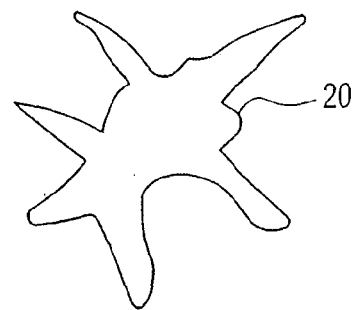
FIG. 4 is an illustration of dendritic cell produced by differentiation of a blood monocyte by the method of the present invention.

As shown in FIG. 2, as the subject's blood is pumped though the plastic channel, monocytes 12 adhere to the inner walls 15 of the plastic channel 10, either directly or by interacting with proteins and/or platelets adhered to the plastic channel. Shear forces are imposed on the adhered monocytes by the fluid flowing past the monocytes and, as shown in FIG. 3, the monocytes 12 become dislodged from the wall 15. As the monocytes flow through the plastic channel, they may undergo several episodes of adherence and removal from the channel walls. As a result of the forces experienced by the monocyte, activation signals are transmitted which cause the monocyte to differentiate and form an immature dendritic cell 20, illustrated in FIG. 4. As discussed above, in one embodiment, the plastic channel is part of a conventional photopheresis apparatus.

As discussed above, after the blood has been passed through the plastic channel, the subject's blood may be incubated in the presence of disease effector agents, such as for example apoptotic cancer cells, to allow phagocytosis of the apoptotic cells and subsequent maturation of the dendritic cells. As the dendritic cell continues to mature during the incubation period, it processes the apoptotic cells. Although not limiting to the present invention, the inventors believe that by the end of the incubation period, the dendritic cell has digested the apoptotic cells, processed the proteins obtained from the apoptotic cellular materials, and is presenting those antigens at the surface of the dendritic cell. After the incubation period, the composition containing the antigen presenting dendritic cells is reinfused into the subject for immunotherapy.

Figure 5:
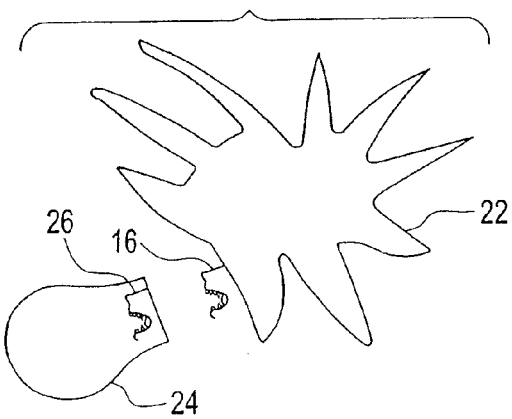
FIG. 5 is an illustration of a dendritic cell which has been reinfused into the subject's bloodstream presenting a class 1 associated peptide antigen to a T-cell.
Figure 6:
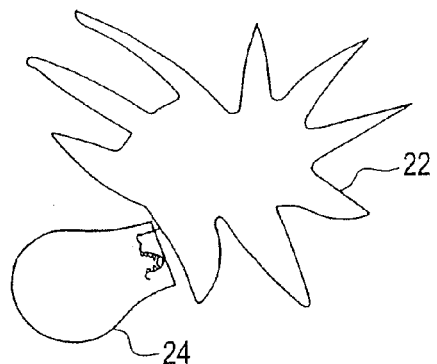
FIG. 6 is an illustration of the class 1 associated peptide antigen presented on the surface of the dendritic cell as it is received by a complementary receptor site on the T-cell.
Figure 7:
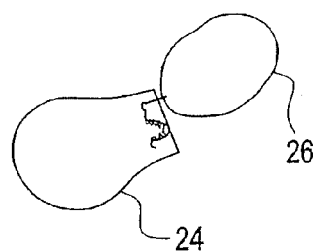
FIG. 7 is an illustration of a clone of the activated T-cell attacking a disease-causing cell displaying the class 1 associated peptide antigen.

Referring now to FIGS. 5 and 6, which illustrate the dendritic cell after reinfusion into the subject's blood stream, the dendritic cell 22 presents at its surface antigens 16 from the cellular material to a healthy T-cell 24 which has a receptor site 26 for the antigen 16. When the healthy T-cell 24 receives the antigen from the dendritic cell, as shown in FIG. 6, the healthy T-cell is activated and induces the formation of T-cell clones which will recognize and attack disease effectors displaying the antigen. As a result, as shown in FIG. 7, the healthy T-cell clones 24 of the subject's immune system are triggered to recognize the antigen displayed by the disease effector agent, and to attack and kill disease cells 26 in the subject which display the same antigen.

Inducing monocyte differentiation according to the method described above provides dendritic cells in numbers which equal or exceed the numbers of dendritic cells that are obtained by expensive and laborious culture of leukocytes in the presence of cytokines such as GM-CSF and IL-4 for seven or more days. The large numbers of functional dendritic cells generated by the method described above provide a ready means of presenting selected material, such as, for example, apoptotic cells, disease agents, antigens, plasmids, DNA or a combination thereof, and are thereby conducive to efficient immunotherapy. Antigen preparations selected to elicit a particular immune response may be derived from, for example, tumors, disease-causing non-malignant cells, or microbes such as bacteria, viruses and fungi. The antigen-loaded dendritic cells can be used as immunogens by reinfusing the cells into the subject or by otherwise administering the cells in accordance with methods known to elicit an immune response, such as subcutaneous, intradermal or intramuscular injection. As described below, it is also possible to generate antigen-loaded dendritic cells by treating and co-incubating monocytes and disease effector agents which are capable of expressing disease associated antigens.

As discussed above, monocyte differentiation is induced by pumping a blood leukocyte preparation containing monocytes through a plastic treatment apparatus. The plastic treatment apparatus used to treat the monocytes to induce monocyte differentiation may be a conventional photopheresis apparatus or alternatively may be a device comprised of any plastic material to which the monocytes will transiently adhere and that is biocompatible with blood leukocyte cells. Examples of materials that may be used include acrylics, polycarbonate, polyetherimide, polysulfone, polyphenylsulfone, styrenes, polyurethane, polyethylene, Teflon or any other appropriate medical grade plastic. In a preferred embodiment of the present invention, the treatment device is comprised of an acrylic plastic.

In the monocyte treatment apparatus, the leukocyte preparation flows through narrow channels. Narrow channels are used to increase the probability and frequency of monocyte contact with the interior plastic surface of the treatment apparatus. The narrow channels also result in flow patterns through the treatment apparatus which impose shearing forces to monocytes transiently contacting or adhering to the interior plastic surfaces of the treatment apparatus.

Figures 8, 9:
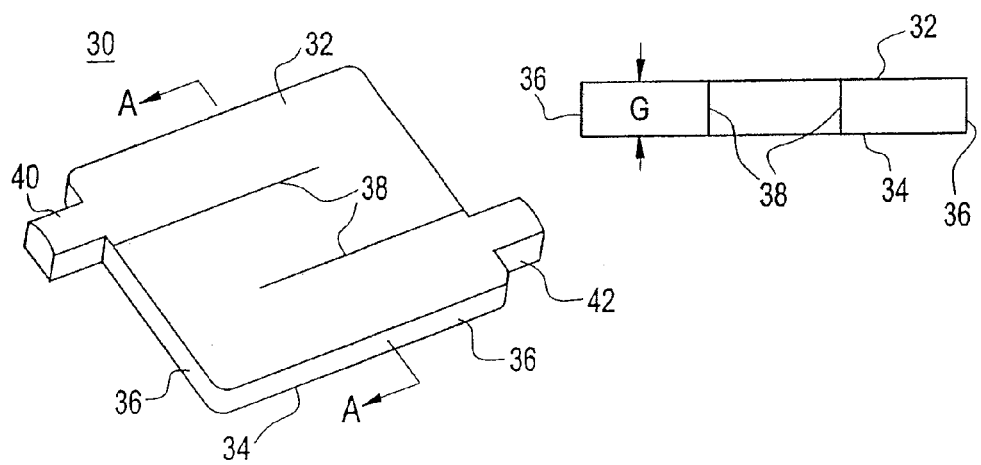
FIG. 8 is a side view of a plastic treatment apparatus which may be used to induce monocyte differentiation into functional antigen presenting dendritic cells.
FIG. 9 is a view of cross section A-A of the plastic treatment apparatus of FIG. 8.

Referring now to FIGS. 8 and 9, one embodiment of a plastic monocyte treatment apparatus is shown. In this embodiment, the treatment apparatus 30 comprises a top plate 32, a bottom plate 34 and side walls 36 to form a box-like structure having a gap, G, between the top plate 32 and the bottom plate 34 to form a narrow channel for flow of blood leukocyte preparations. The top plate 32 and the bottom plate 34 are comprised of a plastic material, such as acrylic or other suitable medical grade plastic as described above.

The side walls 36 of the treatment apparatus may be comprised of the same material as the top plate 32 and the bottom plate 34. Alternatively, the side walls 36 may be comprised of any material, such as for example a rubber, that will form a seal between with the top plate and the bottom plate. The treatment apparatus may have any desired outer shape. For example, the treatment apparatus may have rounded corners, or it may be round or oval.

The top plate 32, bottom plate 34 and side walls 36 may be fastened together using any fastening method known to those skilled in the art. For example, the top plate and bottom plate may be glued to the side walls. Alternatively, bolts, rivets or other fasteners may be used to assemble the top plate, bottom plate and side walls. Gaskets or other sealing materials may be used as necessary to seal the treatment apparatus to prevent leakage.

Internal walls 38 may be provided to direct the flow of the monocytes through the device. The internal walls are typically made of the same material as the top plate and the bottom plate. The internal walls direct the flow of the leukocyte preparation through the treatment apparatus, prevent channeling of flow through the treatment apparatus, and increase the plastic surface area that the monocytes are exposed to within the treatment apparatus. The number of internal walls and the arrangement of the internal walls may be varied to achieve the desired flow pattern through the treatment device. The available surface area may also be increased by including one or more plastic dividers or posts in the flow path through the narrow channels of the plastic treatment apparatus.

The total surface area available for monocyte interaction may also be increased by passing leukocytes through a closed plastic treatment apparatus containing plastic or metal beads. These beads increase the total surface area available for monocyte contact and may be composed of iron, dextran, latex, or plastics such as styrenes or polycarbonates. Beads of this type are utilized commercially in several immunomagnetic cell separation technologies and are typically between 0.001 and 10 micrometers in size, although the invention is not limited in this regard and any appropriate bead may be used. Unmodified beads or those coated with immunoglobulins may also be utilized in this embodiment.

Referring again to FIG. 8, the monocytes enter the treatment apparatus through an inlet connection 40, flow through the treatment apparatus and exit through an outlet connection 42. A pump (not shown) may be used to induce flow through the treatment apparatus, or the treatment apparatus may be positioned to allow gravity flow through the treatment apparatus. The inlet connection 40 and outlet connection 42 may be separate components that are fastened to the treatment apparatus, or they may be made of the same material as the treatment apparatus and formed as an integral part of the top and bottom plates or the side walls.

The top plate 32 and the bottom plate 34 are spaced apart to form a gap G that is preferably between about 0.5 mm and about 5 mm. The total volume of the treatment apparatus is preferably between 10 ml and about 500 ml but may vary depending on the application and blood volume of the mammalian species. Preferably, the leukocyte fraction is pumped through the treatment apparatus at flow rates of between about 10 ml/min and about 200 ml/min. Shearing forces are typically in the range associated with mammalian arterial or venous flow but can range from 0.1 to 50 dynes/cm$^2$. The invention is not limited in this regard, and the volume of the treatment apparatus and the flow rate of the leukocyte preparation through the treatment apparatus may vary provided that sufficient shearing forces are imposed on monocytes contacting the walls of the treatment apparatus to induce monocyte differentiation into functional dendritic cells.

The interior surfaces of the treatment device may be modified to increase the available surface area to which the monocytes are exposed. The increased surface area increases the likelihood that monocytes will adhere to the interior surface of the treatment apparatus. Also, the modified surface may influence the flow patterns in the treatment apparatus and enhance the shearing forces applied to monocytes adhered to the interior surface by the fluid flowing through the treatment apparatus. The interior surfaces of the treatment apparatus may be modified by roughening the surface by mechanical means, such as, for example, by etching or blasting the interior surfaces using silica, plastic or metal beads. Alternatively, grooves or other surface irregularities may be formed on the plastic surfaces during manufacturing. The enclosed exposure area through which the monocytes flow may also consist of a chamber whose contents include beads of various compositions to maximize surface area exposure. The invention is not limited in this regard, and the interior surface or contents of the treatment apparatus may be by any other appropriate method known to those skilled in the art.

As will be recognized by those skilled in the pertinent art based upon the teachings herein, numerous changes and modifications may be made to the above-described embodiments of the invention without departing from its scope as defined in the appended claims. Accordingly, this detailed description of preferred embodiments is to be taken in an illustrative as opposed to a limiting sense.

What is claimed is:

1. A method for producing functional dendritic cells comprising the steps of:
   (a) obtaining an extracorporeal quantity of a subject's blood;
   (b) treating the extracorporeal quantity of blood to separate the blood into a plasma component containing proteins, a platelet component and a buffy coat component;
   (c) providing a plastic treatment device having plastic channels;
   (d) pumping the plasma component containing proteins through the plastic treatment device;
   (e) after the plasma component has been pumped through the plastic treatment device, pumping the platelet component through the plastic treatment device;
   (f) after the platelet component has been pumped through the plastic treatment device, pumping the buffy coat component through the plastic treatment device and recovering the buffy coat component after it has been pumped through the plastic treatment device.

2. The method of claim 1, wherein the plastic treatment device allows transmittance of light to the interior of the plastic device and is combined with a light source that produces light of a wave length selected to activate a selected photoactivatable agent further comprising the steps of:
   (g) adding a photoactivatable agent that will render disease effector cells apoptotic to the extracorporeal quantity of blood prior to separating the blood into a plasma component, a platelet component and a buffy coat component; and (h) irradiating the plasma component, a platelet component and a buffy coat component using the light source during treatment in the plastic treatment device.

3. The method of claim 2, wherein the photoactivatble agent is 8-MOP.

4. The method of claim 3, wherein the plastic treatment device is a photopheresis device.

5. The method of claim 1, wherein the plasma component is pumped through the plastic treatment device for a period of between about 1 minute and 60 minutes.

6. The method of claim 5, wherein the platelet component is pumped through the plastic treatment device for a period of between about 5 minutes and 30 minutes.

7. The method of claim 6, further comprising the steps of:

(g) pumping the buffy coat component through the plastic treatment device at a flow rate such that monocytes contained in the buffy coat component adjacent to the wall of the plastic treatment device are exposed to a shear force of between about 0.1 to about 0.5 dynes/cm$^2$; and (h) increasing the flow rate of the buffy coat component through the plastic treatment device such that monocytes contained in the buffy coat component adjacent to the wall of the plastic treatment device are exposed to a shear force of between about 1 to about 50 dynes/cm$^2$.

8. The method of claim 5, wherein flow of the plasma component through the plastic treatment device is stopped for a period of time to allow the plasma proteins to adhere to the surfaces of the plastic treatment device.

9. The method of claim 1, further comprising the step of incubating the recovered buffy coat component for a sufficient time to allow the formation of functional dendritic cells.

10. The method of claim 1, further comprising the step of reinfusing the buffy coat component to the patient after the buffy coat component has been pumped through the plastic treatment device.

11. The method of claim 2, further comprising the steps of recovering the buffy coat component after it has been pumped through the plastic treatment device, and incubating the recovered buffy coat component for a sufficient time to allow the formation of functional dendritic cells and to allow the dendritic cells to phagocytize apoptotic disease effector cells.

12. The method of claim 1, further comprising the step of (g) incubating the recovered buffy coat component with apoptotic disease effector cells for a sufficient time to allow the formation of functional dendritic cells and to allow the dendritic cells to phagocytize the apoptotic disease effector cells.

* * * * *